(12) United States Patent
Colvin

(10) Patent No.: US 6,218,951 B1
(45) Date of Patent: Apr. 17, 2001

(54) SAFETY CIRCUIT

(75) Inventor: Donald Colvin, Mukliteo, WA (US)

(73) Assignee: Western Technology, Seattle, WA (US)

( * ) Notice: Subject to any disclaimer, the term of this patent is extended or adjusted under 35 U.S.C. 154(b) by 0 days.

(21) Appl. No.: 09/240,968

(22) Filed: Jan. 29, 1999

(51) Int. Cl.[7] .................................................. G08B 21/00
(52) U.S. Cl. .......................... 340/635; 340/632; 340/628
(58) Field of Search .................................. 340/635, 636, 340/632, 628, 605, 618; 324/694; 73/60, 290 R, 292

(56) References Cited

U.S. PATENT DOCUMENTS

| | | |
|---|---|---|
| 3,778,799 | 12/1973 | Bendayan . |
| 4,788,529 | 11/1988 | Lin . |
| 5,517,181 | 5/1996 | Gray et al. . |
| 5,546,009 * | 8/1996 | Raphael ................................ 324/694 |
| 5,565,853 | 10/1996 | Jun-Young . |
| 5,801,634 | 9/1998 | Young et al. . |

\* cited by examiner

*Primary Examiner*—Julie Lieu
(74) *Attorney, Agent, or Firm*—Frost Brown Todd LLC

(57) ABSTRACT

A safety circuit permits the operation of a device when the device is located in a safe operating environment. There is a power supply that supplies power to the sensor and to the logic circuits. The sensor could be one of any number of sensors depending on the environment variable which it is desired to detect or monitor and the size of the space for the detector to fit in. The logic circuits use the signal from the sensor to determine when a safe condition exists. When the logic circuits determine that a safe environment is present, the logic circuits send a signal to the power control circuit, which will permit the operation of the device, which if operated in an unsafe environment could endanger personnel and/or property. The results of operating a device in an unsafe environment could include, but are not limited to, fire; explosion; injury or death of personnel, or any other undesirable event.

7 Claims, 4 Drawing Sheets

SAFETY CIRCUIT

This is a non-provisional application based on an earlier filed provisional application, Ser. No. 60/873,501 filed Jan. 30, 1998.

BACKGROUND OF THE INVENTION

1. Field of the Invention

This invention relates generally to devices used to detect the presence of toxic, explosive or otherwise dangerous gases; temperature; humidity; light; particulate; or other environment parameters, and more particularly to devices used to detect the presence of toxic, explosive, or dangerous gases; temperature; humidity; light; or other environment parameters and permit the operation or actuation of a device when the monitored environmental parameter is in the safe range.

2. Description of the Related Art

Toxic and explosive gas detectors have been used in many different areas. The first gas detector was probably the canary used in mining to indicate toxic atmospheres. Since the use of the canary began there have been many developments in gas detecting technology. Currently gas detectors are used to detect the presence of propane, carbon monoxide, gasoline vapors, hydrogen, oxygen and other gases. Typical sensor or detector locations are: 1) the bilge of a recreational or commercial vessel; 2) the inside of a house; 3) enclosed spaces prior to entry; and 4) areas where dangerous gases may be present due to manufacturing or transportation.

The detectors currently on the market merely provide an indication that a hazard is present or a value of the environmental parameter monitored or measured. This indication may be a warning alarm, a warning light, or meter indication. However, these detectors will not take any other action to prevent an explosion, fire, injury, death, or property damage in the event that an unsafe environment exists. The inability of these detectors to either act in the event an unsafe condition is detected or to permit action only when the environment is safe results in unnecessary injuries, deaths, and damage or destruction of valuable property by fire, explosion, toxic gas, or other environmental hazards.

SUMMARY OF THE INVENTION

The present invention has solved the problems cited above and generally comprises a safety circuit. There is a power supply that supplies power to the sensor and to the logic circuits. The sensor could be one of any number of sensors depending on the environment variable which it is desired to detect or monitor and the size of the space for the detector to fit in. The logic circuits use the signal from the sensor to determine when a safe condition exists. When the logic circuits determine that a safe environment is present, the logic circuits send a signal to the power control circuit which will permit the operation of a device which, if operated in an unsafe environment could endanger personnel and/or property. The results of operating a device in an unsafe environment could include, but are not limited to, fire; explosion; injury or death of personnel, or any other undesirable event.

The unsafe environments include, but are not limited to, the presence of hazardous temperature; light; high or low humidity; excessive vibration; smoke; toxic, explosive, flammable, or other dangerous gas; or toxic, explosive, flammable, or other hazardous particulate.

BRIEF DESCRIPTION OF THE DRAWINGS

The accompanying drawings incorporated in and forming a part of the specification illustrate several aspects of the present invention, and together with the description serve to explain the principles of the invention. In the drawings.

Reference will now be made in detail to the present preferred embodiment of the invention, an example of which is illustrated in the accompanying drawings.

DETAILED DESCRIPTION

1. Overview

The purpose of the safety circuit is to permit operating an electrical or other device when the device is in a safe environment. The environmental parameters that could be monitored include, but are not limited to, pH, temperature, humidity, gas concentration, particulate concentration, conductivity, resistance, electrical charge, light intensity, salinity, radiation, and any other environmental parameter capable of being measured. The sensor will typically be a gas sensor. Although any type of gas may be sensed, typically the gases may be: propane vapor, gasoline vapor, hydrogen, oxygen, other explosive or flammable gases; or carbon monoxide, freon, or other toxic gases.

This system uses a regulated power supply to provide power to both the logic circuit and to the sensor. The sensor provides an output signal which will vary depending on the environmental parameter that the sensor is designed to detect. The logic circuit receives the signal from the sensor. When the logic circuit detects a signal indicating that a safe environment is present, the logic circuit will indicate a safe condition to the power control circuitry. A safe environment is an environment where the environmental variable being monitored is safe for both personnel and the equipment (which the safety circuit controls) to operate. Upon receiving an indication of a safe condition, (including proper and safe operation of the safety circuit) the power control circuit will act to permit the operation of the electrical or other device that is controlled by the safety circuit. A safe condition is a safe environment together with the proper and safe operation of the safety circuit. For example, if a safety circuit with an explosive gas sensor was installed in a portable drill, and if the operator inadvertently took the portable electric drill into an area which had an explosive concentration of propane gas, the circuit would prevent the drill from being operated by preventing the electricity from reaching the motor.

2. Description of the Functional Block Diagram

Figure 1:
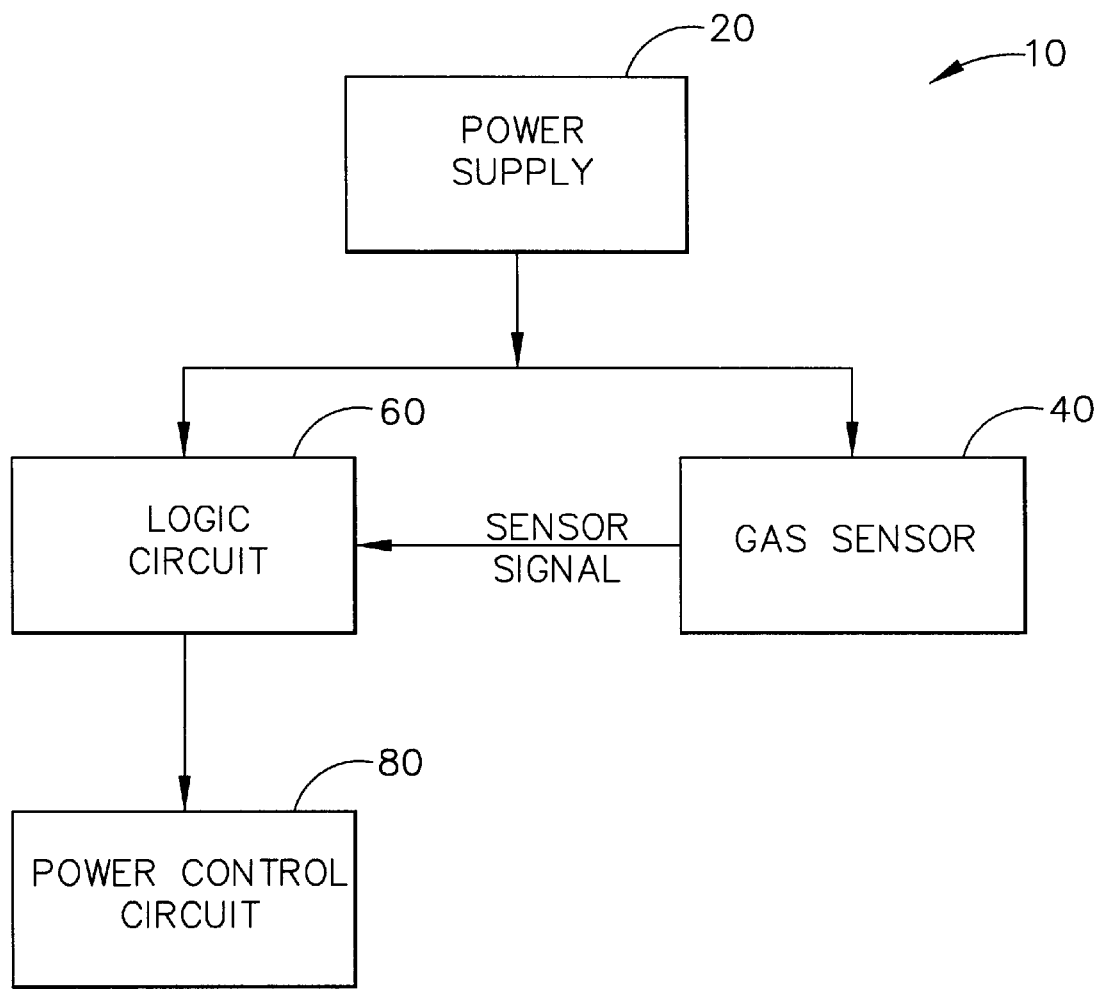
FIG. 1 is a functional block diagram in accordance with the present invention.

Referring now to the drawings in detail, wherein like numerals indicate the same elements throughout the views, FIG. 1 shows a block diagram of safety circuit 10. Safety circuit 10 is comprised of the following functional blocks: power supply 20, sensor 40, logic circuit 60, and control circuit 80.

Power supply 20 supplies the power to both sensor 40 and logic circuit 60. Power supply 20 typically provides the proper voltage for both logic circuit 60 and sensor 40. Logic circuits typically operate on between 3 and 5 volts and thus power supply 20 should provide an output at the proper voltage for the logic circuits utilized. Additionally, sensors 40 utilized with this circuit typically have voltage requirements from 5 to 25 volts dc. However some sensors that may be interfaced with this circuit may require different voltages. Therefore, power supply 20 will typically have a second voltage output if the sensor 40 requires a different voltage than the logic circuit 60.

Sensor 40 is any sensor that is required or desired to be used in a specific application. Typically, a single sensor will be used, however, there are safety circuits that can effectively use two or more sensors connected either in series or parallel. When two or more sensors 40 are employed, the sensors 40 may be identical sensors 40 placed in two different locations so that a larger area is monitored. Alternatively, the sensors 40 may monitor two different environmental variables, for example, both a conductivity sensor 40 and a pH sensor 40 could be used to monitor a steam system for proper operation. Typically, the sensor 40 selected will be used to detect an explosive gas mixture in the atmosphere. There are, however, applications for sensors capable of detecting other environmental parameters. For example: using a toxic gas sensor on the safety circuit to prevent inadvertent entry to a room into which a toxic gas has leaked; or using both temperature and humidity sensors in the safety circuit to shut down a steam system on indications of a steam rupture.

Logic circuit 60 contains the appropriate circuits necessary to determine when a safe environment is present based on the signal provided by the sensor. Since this is a safety device, it is preferred that the logic circuit use redundant logic subcircuits. Additionally, since this is a safety circuit each logic subcircuit should provide an affirmative signal indicating that the environmental parameter measured is in the safe range. When the environment is safe and all the upstream portions of the circuit are operating properly the output of the logic circuit is a signal which will cause the power control circuit 80 to permit the device to which the safety circuit 10 is attached from operating. Typically the safety circuit 10 will be used in or on an electric device and the power control circuit 80 would permit the electrical power to energize this device.

3. Circuit Diagram

Figure 2:
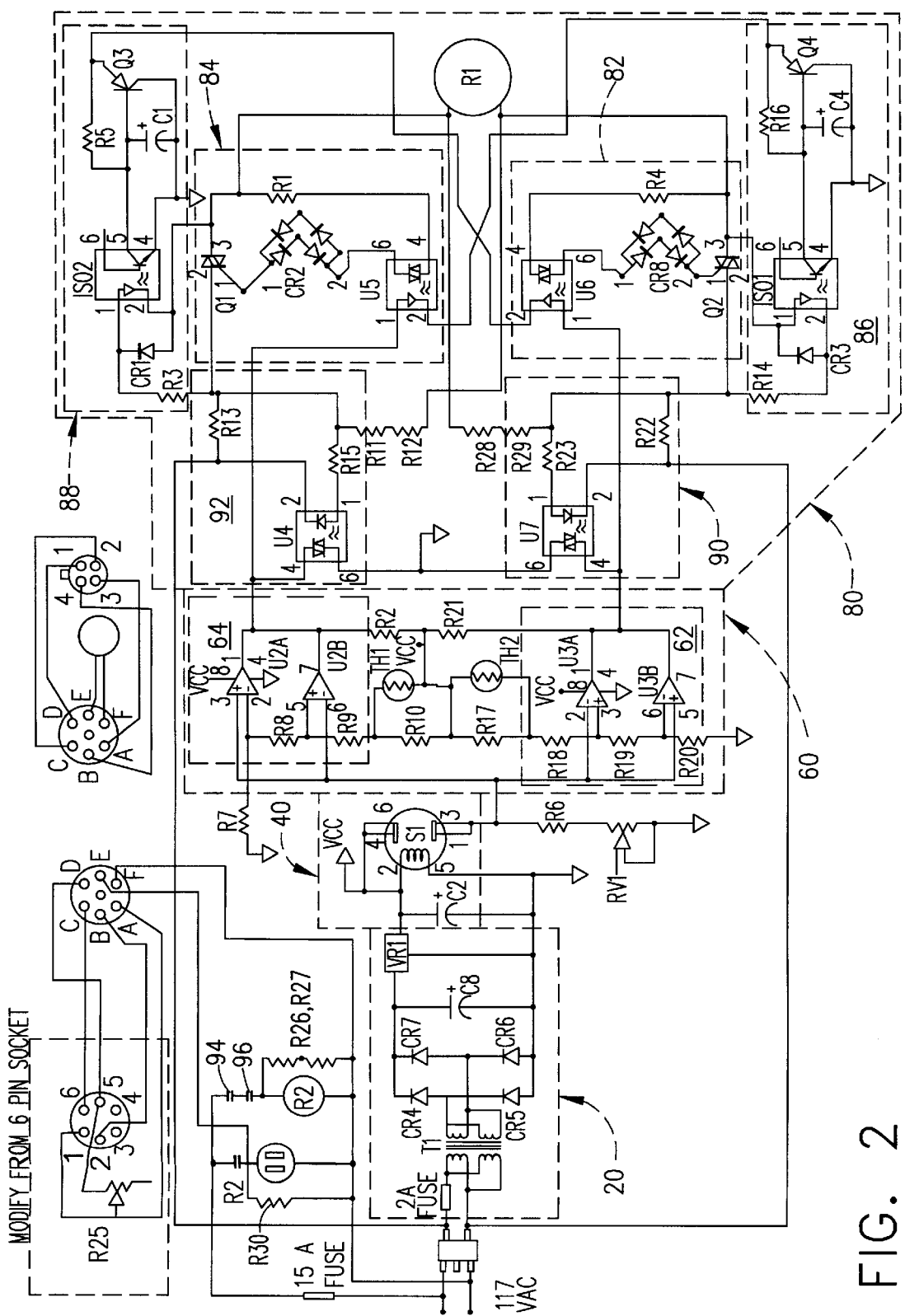
FIG. 2 is an electrical schematic of the preferred embodiment of the present invention.

FIG. 2 provides a circuit diagram for the preferred embodiment of a safety circuit 10 in accordance with the present invention. The safety circuit 10 has the same basic components as shown in the functional block diagram (FIG. 1). These components are: power supply 20, sensor 40, logic circuit 60, and power control circuit 80.

Power supply 20 is a regulated power supply that typically supplies a relatively constant voltage to the sensor 40 and logic circuit 60. The power supply is designed to provide the appropriate power level for the sensor 40, the logic circuit 60, and if required, the appropriate voltage for the rest of the electrical circuit; including, the power control circuit 80. In the preferred embodiment power control circuit 80 does not use any power from the power supply 20. Control circuit 80 receives its power directly from the same source as the device which safety circuit 10 controls. Sensor 40 will use the output of power supply 20 to provide power for the sensing element and, if required, for a heating or other element of the sensor. Power supply 20 also provides power to the op amps and to the resistors used in a voltage divider to set a "safe" window voltage to which the output of sensor 40 is compared in logic circuit 60. The design and manufacturing of regulated power supplies providing specific output voltages is well known and thus will not be described in detail.

Figure 3A:
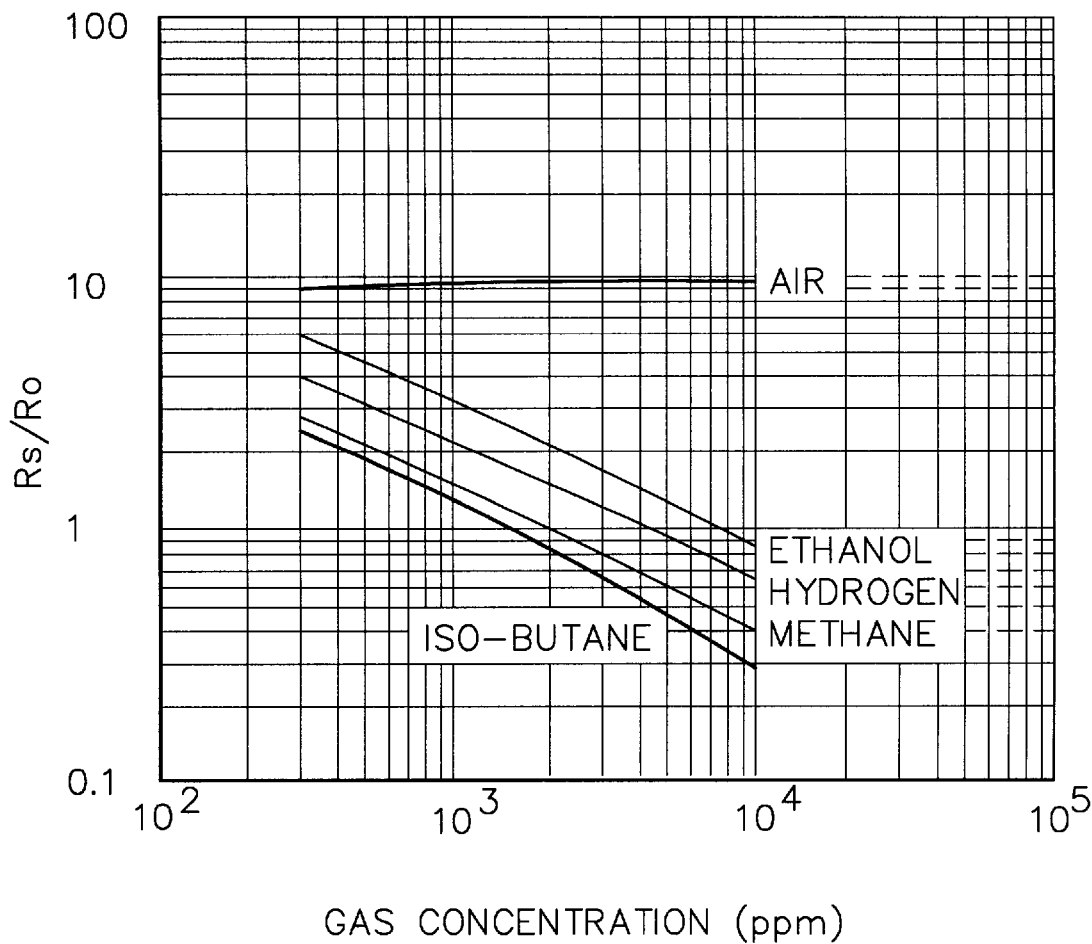
FIG. 3A is a sample response curve for a sensor used to detect combustible gases.
Figure 3B:
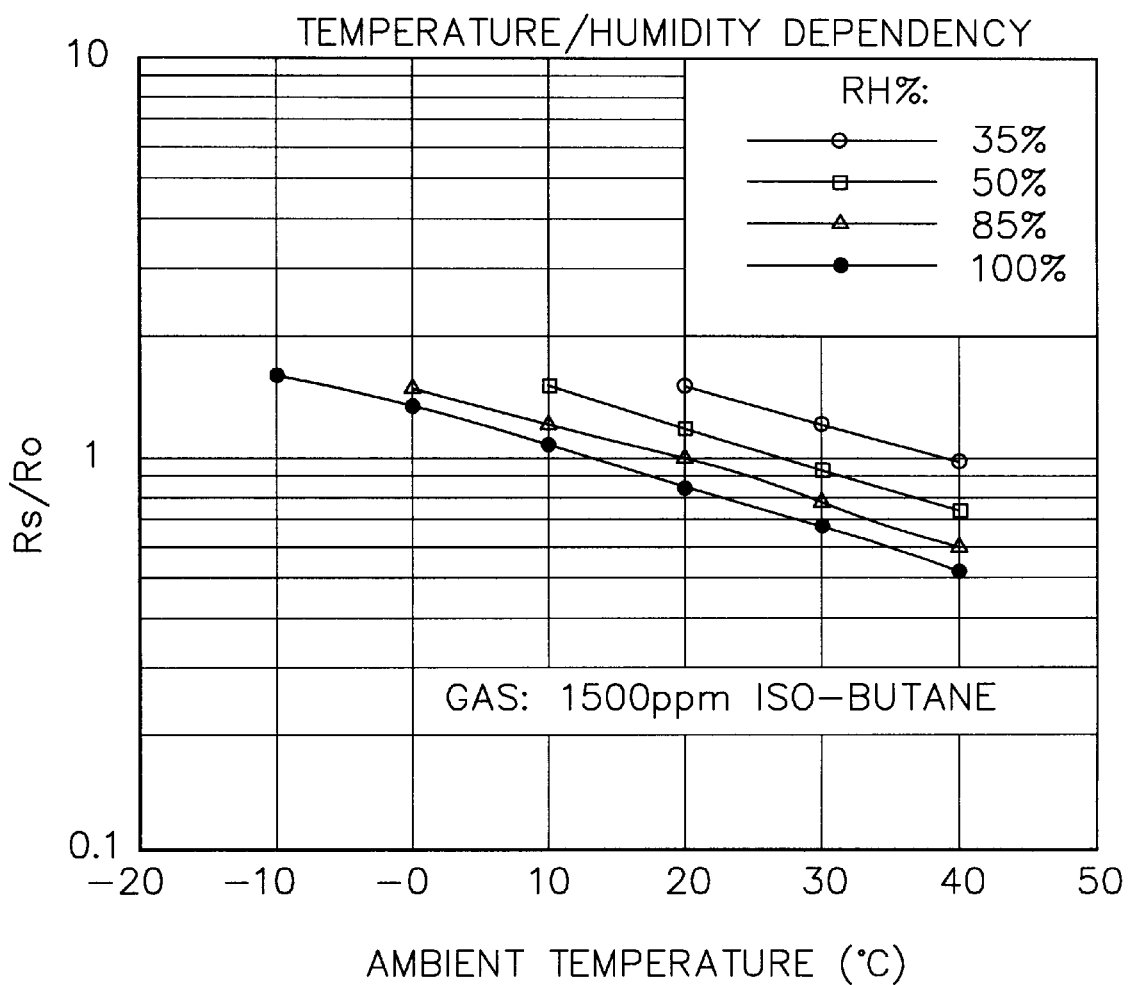
FIG. 3B is a sample temperature/humidity dependency curve associated with the sensor response curve shown in FIG. 3A.

The sensor 40 samples the environment around the sensor and provides a detection signal to the logic circuit 60. Sensors 40 that are used to detect flammable or explosive atmospheres typically have a heating element which maintains the sensor at a specific temperature and a sensing element whose resistance varies with the concentration of flammable or burnable materials in the atmosphere. FIG. 3A shows a typical response curve for a combustible gas sensor. The resistance of this sensor lowers as the concentration of a combustible gas increases. The resistance of the sensing element of the sensor 40 will determine voltage of the signal that is input to the logic circuit 60. Additionally, the resistance of the sensing element in combustible gas sensors will vary with the temperature/humidity of the air around the sensor as shown in FIG. 3B. Thus, the voltage of the output signal from sensor 40 will depend upon the environment around the sensor and the input voltage from power supply 20. During safe conditions, the voltage of the output signal from sensor 40 stays within a relatively narrow band.

Since this is a safety circuit, logic circuit 60 is formed primarily from two identical LM393 window comparators 62, 64. Each window comparator has two op amps that are wired in a logical "or" configuration. The voltage range over which the comparators 62, 64 will produce a high output is determined by the values selected for resistors R7, R8, and R9 for comparator 64 and resistors R18, R19, and R20 for comparator 62. Some sensors 40 used to measure environmental parameters other than temperature have output voltages that are subject to undesired temperature variations (FIG. 3B). If the output voltage of sensor 40 is subject to undesired temperature variations, then a thermistor TH1 is added to resistors R7, R8, and R9 to shift the "safe" voltage window for comparator 64 to compensate for the temperature dependence of sensor 40. Similarly, a thermistor TH2 is added to resistors R18, R19, and R20 for comparator 62. It is preferred that the temperature response curve of thermistors TH1 and TH2 compensate for the temperature dependency of sensor 40 over the expected operating temperatures of safety circuit 10. When the voltage output of the gas sensor 40 is in the safe range, the output of both window comparators will be high. When the voltage output of the sensor 40 is outside the "safe" window the logic circuit will act as if an unsafe environment existed. Thus, the output of one or both window comparators 62, 64 will be low when the voltage output from sensor 40 is outside the "safe" window. For example, in the present circuit the voltage output of a sensor 40 may fall below the safe range either due to a failure of sensor 40 or power supply 20, or due to a low voltage condition. When the voltage input to window comparators 62, 64 is below the safe window the output of op amp U2A of comparator 64 and op amp U3A of comparator 62 will go low, forcing the output of each window comparator 62, 64 to be low. Thus, the output of logic circuit 60 to power control circuit 80 will be low. Alternately, when the sensor 40 is a combustible gas sensor and, senses an unsafe condition, the sensor's 40 output voltage increases due to the explosive or flammable gas in the atmosphere reducing the resistance of the sensing element in sensor 40, With the voltage input to comparators 62, 64 is above the "safe" window, the output of op amp U3B of comparator 62 and U2B of comparator 64 will go low with the same result as discussed above when op amps U2A and U3A go low.

Power control circuit 80 is also constructed in a redundant fashion. Power circuit 80 has two switch circuits 82, 84; two triac pulse detection circuits 86, 88; two over current protection circuits 90, 92; an one IDEC RSSAN relay R1. Only one relay R1 is used, since a failure of relay R1 would cause the circuit to fail in a safe manner by preventing the operation of the equipment attached to or controlled by safety circuit 10. Switch circuit 82 is coupled to and receives an input from window comparator 62 and switch circuit 84 is coupled to and receives an input from window comparator 64. When there are no faults within power control circuit 80, and a "safe" condition exists, a high output (safe condition) from the comparator 62 will actuate switch circuit 82 and a high output (safe condition) from comparator 64 will actuate switch circuit 84. Both switch circuits 82 and 84 are coupled to and provide a low resistance current path to relay R1. When both switch circuits 82 and 84 are triggered, current will flow to relay R1 causing relay R1 to energize, closing contacts 94 that will permit the electric or other device to which safety circuit 10 is connected to operate. Additionally, the preferred embodiment has an ARTISAN 436 U.S.A. time delay relay (not shown). This relay typically has a one minute time delay upon energizing the circuit 10 and time delay relay. This one minute time delay will prevent erroneous response of safety circuit 10 while circuit 10 is warming up. Additionally there is a two minute time delay after safety circuit 10 removes power from the device due to the detection of an unsafe condition.

Switch circuits 82 and 84 are triggered by high outputs from window comparators 62, 64 of logic circuit 10. For example, a high output form window comparator 62 will cause current to flow through a H11J3 opto-isolator U6 provided that pulse detection circuit 88 is sensing pulses across triac Q2. Thus, a voltage will be applied to diac CR8, when the voltage applied to diac CR8 reaches diac's CR8 break over voltage, diac CR8 will allow current to flow through diac CR8 and trigger triac Q2. Diac means either a diac or an assembly of diodes or other devices that will permit a large enough voltage to develop across the triac, during the portion of the AC cycle when the opto-isolator is forward biased, to trigger the opto-isolator before the triac is triggered. When triac Q2 is triggered, triac Q2 will permit current flow through triac Q2. Since this circuit uses an AC power source, triac Q2 will pulse because diac CR8 will not constantly trigger triac Q2.

As a further safety feature there are two triac pulse detection circuits 86, 88. These circuits sense the voltage across the triac in each switch circuit 82, 84. The pulse detection circuit 86 senses the voltage across triac Q2 in switch circuit 82 and pulse detection circuit 88 senses the voltage across triac Q1 in switch circuit 84. When switch circuit 82 is activated the voltage across the triac Q2 will pulse, indicating that the triac Q2 has been triggered and is functioning properly. The triac Q1 in switch circuit 84 will behave in a similar manner. When detection circuit 86 detects that triac Q2 of switch circuit 82 is turned on and functioning properly, the detection circuit 86 will permit switch circuit 84 to be activated. Similarly, when detection circuit 88 detects that triac Q1 of switch circuit 84 is triggered and functioning properly, the detection circuit 88 will permit switch circuit 82 to be activated.

For example, when triac Q1 pulses there is a time period where triac Q1 has a voltage difference and a time period when triac Q1 does not have a voltage difference across triac Q1. When there is a voltage difference across triac Q1, a 4933 opto-isolator IS02 will permit current flow. Thus, a 1RE capacitor C1 will discharge and the voltage between the base of and the collector of a 2N3906 transistor Q3 will permit current to flow through transistor Q3. With current flowing through transistor Q3, current will flow through opto-isolator U6 to ground. When triac Q1 is permitting current to flow, there will not be a voltage difference across triac Q1. Thus, opto-isolator IS02 will prevent current to flow through opto-isolator IS02 to ground and capacitor C1 will recharge. During the initial portion of the capacitor's C1 recharge the voltage between the base and the collector of transistor Q3 will be low enough that transistor Q3 will continue to permit current to flow through transistor Q3. Capacitor C1 is sized to accommodate the pulse length of the triac Q1 selected, so that before the voltage rise across capacitor C1 is sufficient to turn off transistor Q1, the triac Q1 has a voltage across the triac Q1 and capacitor C1 is discharged.

However, if triac Q1 stops pulsing but does not have a voltage drop across the triac Q5, then the capacitor C1 will continue to charge and the voltage across capacitor C1 and across the base and collector of transistor Q3 will increase until transistor Q3 turns off. With no current passing through transistor Q3, no current will flow through opto-isolator U6 resulting in switch circuit 82 turning off or preventing switch circuit 82 from turning on. Pulse detection circuit 86 will operate in a similar fashion to that described above. If the detection circuit 86 does not detect a pulsing voltage across triac Q2, then the pulse detection circuit 86 would prevent switch circuit 84 from accuating or turn off switch circuit 84 if this circuit was already operating.

If there is a short or fault within power control circuit 80 which causes a high current within control circuit 80, then either or both current protection circuits 90, 92 will operate to protect power control circuit 80. Protection circuit 90 protects power control circuit 80 by shunting the output from window comparator 62 to ground. The shunting of the output from window comparator 62 to ground will cause switch circuit 82 to see a low input, which results in switch circuit 82 turning off. Similarly, protection circuit 92 will cause switch circuit 84 to turn off.

For example, the current protection circuit 90 operates by using the voltage developed across resistor R22 to trigger a H11J3 opto-isolator U7. Resistor R22 is selected so that when the current through resistor R22 exceeds safe levels then the voltage across resistor R22 will trigger opto-isolator U7. When U7 is triggered the output of window comparator 62 of logic circuit 60 is stunted to ground with the result described above 4. Operation a. Normal Operation The power supply 20 provides power to gas sensor 40 and to logic circuit 60. Sensor 40 will provide a steady or relatively steady output signal to logic circuit 60. This signal will fall within the "safe" voltage window of the window comparators 62, 64 of logic circuit 60. The window comparators 62, 64 will produce a high output which accuates switch circuits 82, 84 of power control circuit 80. Upon accuation of both switch circuits 82, 84 relay R1 is energized. Energizing relay R1 will permit the device to which the circuit is attached to function.

b. Low Voltage

When there is a low voltage supplied to power supply 20, the voltage regulator VR1 fails to provide a high enough voltage, or sensor 40 fails to send an output signal, then the voltage input to window comparators 62, 64 of logic circuit 60 will be below the "safe" voltage window. This input to window comparators 62, 64 will result in an overall low output from window comparators 62, 64 resulting in a low signal to switch circuits 82 and 84 of power control circuit 80. A low input to switch circuits 82 and 84 will prevent these circuit from operating or if operating to turn off. When switch circuits 82 or 84 are off relay RI will be deenergized and the contacts in the motor controller for the electric device will remain open and the device will not start.

c. High Current in Power Control Circuit 80

When over-current protection circuit 90 detects an over current condition it shunts the output from the window comparator 62 to ground. As a result of this shunt switch circuit 82 will see a low input and will turn off. When switch circuit 82 is off relay R1 will be deenergized with the results as described above Over protection circuit 92 will function in a similar manner to that described above. High current in power control circuit 80 would typically be caused by a short circuit or a fault to ground within the circuit.

d. Dangerous Concentration of Gas Present

In the event that there is an unsafe environment detected by that gas sensor 40, sensor 40 will typically produce a high voltage output that will be above the "safe" voltage window of window comparators 62, 64. A voltage input to logic circuit 60 above the "safe" voltage window for comparators 62, 64 will cause window comparators 62, 64 to have a low output with the results described above.

e. Short Across a Triac

If a short develops across triac Q2 of switch circuit 82 either due to a failure or due to an over voltage condition, then the pulse detection circuit 86 will not detect the pulsing of the triac Q2. When detection circuit 86 no longer detects the pulsing of the triac Q2, then the detection circuit 86 will prevent switch circuit 84 from operating. Without both switch circuits 82, 84 operating, relay R1 will be de-energized and, as a result, the attached electrical device will either shut down or not be permitted to start. A short across triac Q1 of switch circuit 84 would cause detection circuit 88 to act in a similar fashion and produce similar results.

In summary, numerous benefits have been described which result from employing the concepts of the invention. The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A safety circuit comprising:
   at least one sensor, said at least one sensor capable of measuring at least one parameter of the environment around said at least one sensor, each of said at least one sensor further comprising a sensing element, the resistance of said sensing element adapted to vary with the concentration of flammable or burnable materials in the atmosphere;
   a logic circuit, said logic circuit coupled to an output of said sensor, said logic circuit capable of detecting when a said output of said sensor is in a safe range, said logic circuit being comprised of first and second window comparators; and
   a power control circuit, said power control circuit coupled to an output of said logic circuit, said power control permitting the operation of a device to which said safety circuit is coupled when said power control circuit receives a safe output signal from said logic circuit.

2. The safety circuit of claim 1 wherein each window comparator comprises two op amps wired in a logical "or" configuration.

3. The safety circuit of claim 2 wherein said power control circuit further comprises two over current protection circuits.

4. The safety circuit of claim 3 wherein said power control circuit further comprises one IDEC RSSAN relay.

5. A safety circuit comprising:
   at least one sensor, said at least one sensor capable of measuring at least one parameter of the environment around said at least one sensor, each of said at least one sensor further comprising a sensing element, the resistance of said sensing element adapted to vary with the concentration of flammable or burnable materials in the atmosphere;
   a logic circuit, said logic circuit coupled to an output of said sensor, said logic circuit capable of detecting when a said output of said sensor is in a safe range; and
   a power control circuit, said power control circuit coupled to an output of said logic circuit, said power control permitting the operation of a device to which said safety circuit is coupled when said power control circuit receives a safe output signal from said logic circuit, said power control circuit comprising two switch circuits.

6. The safety circuit of claim 5 wherein said power control circuit further comprises two triac pulse detection circuits.

7. A safety circuit comprising:
   at least one sensor, said at least one sensor capable of measuring at least one parameter of the environment around said at least one sensor, each of said at least one sensor further comprising a sensing element, the resistance of said sensing element adapted to vary with the concentration of flammable or burnable materials in the atmosphere, said resistance of said sensing element varying with the ambient temperature and humidity of the atmosphere surrounding said at least sensor, said at least one sensor further being adapted to be subjected to undesired temperature variations;
   a logic circuit, said logic circuit coupled to an output of said sensor, said logic circuit capable of detecting when a said output of said sensor is in a safe range, said logic circuit comprising a thermistor added to a plurality of resistors adapt to shift the voltage window for a corresponding comparator; and
   a power control circuit, said power control circuit coupled to an output of said logic circuit, said power control permitting the operation of a device to which said safety circuit is coupled when said power control circuit receives a safe output signal from said logic circuit.

* * * * *